United States Patent
Wallace et al.

(10) Patent No.: US 7,494,776 B2
(45) Date of Patent: Feb. 24, 2009

(54) LABELED COMPLEMENTARY OLIGONUCLEOTIDES TO DETECT OLIGONUCLEOTIDE-LINKED LIGANDS

(75) Inventors: Robert Bruce Wallace, Escondido, CA (US); M. Parameswara Reddy, Brea, CA (US); Kurt Brillhart, Mission Viejo, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 362 days.

(21) Appl. No.: 11/177,766

(22) Filed: Jul. 7, 2005

(65) Prior Publication Data

US 2007/0009914 A1 Jan. 11, 2007

(51) Int. Cl.
  C12Q 1/68 (2006.01)
  G01N 33/53 (2006.01)
(52) U.S. Cl. .................................. 435/6; 435/7.1
(58) Field of Classification Search .................. None
  See application file for complete search history.

(56) References Cited

U.S. PATENT DOCUMENTS

| | | | | |
|---|---|---|---|---|
| 5,112,736 | A | 5/1992 | Caldwell et al. | 435/6 |
| 5,622,826 | A | 4/1997 | Varma | 435/6 |
| 5,648,213 | A | 7/1997 | Reddy et al. | 435/6 |
| 6,103,537 | A | 8/2000 | Ullman et al. | 436/526 |
| 6,117,631 | A | 9/2000 | Nilsen | 436/6 |
| 6,146,833 | A | 11/2000 | Milton | 435/6 |
| 6,303,325 | B1 | 10/2001 | Mehta et al. | 435/7.5 |
| 6,506,594 | B1 | 1/2003 | Barany et al. | 435/287.2 |
| 6,511,809 | B2 | 1/2003 | Baez et al. | 435/6 |
| 6,576,422 | B1 | 6/2003 | Weinstein et al. | 435/6 |
| 6,589,778 | B1 | 7/2003 | Hawkins | 435/287.2 |
| 2002/0051986 | A1 | 5/2002 | Baez et al. | 435/6 |
| 2003/0087271 | A1 | 5/2003 | Ebersole et al. | 435/6 |
| 2003/0092062 | A1 | 5/2003 | Reddy et al. | 435/7.1 |
| 2003/0092901 | A1 | 5/2003 | Farooqui et al. | 536/23.4 |
| 2004/0023271 | A1 | 2/2004 | Kurn et al. | 435/6 |
| 2004/0048311 | A1 | 3/2004 | Ault-Riche et al. | 435/7.1 |
| 2004/0053217 | A1 | 3/2004 | Rothschild et al. | 435/5 |
| 2004/0058385 | A1 | 3/2004 | Abel et al. | 435/7.1 |
| 2004/0121382 | A1 | 6/2004 | Liu et al. | 435/6 |
| 2004/0180362 | A1 | 9/2004 | Lazar et al. | 435/6 |
| 2004/0198969 | A1 | 10/2004 | Baldwin et al. | 536/23.5 |
| 2004/0209261 | A1 | 10/2004 | Keys et al. | 435/6 |

FOREIGN PATENT DOCUMENTS

| | | |
|---|---|---|
| EP | 0 543 222 A1 | 5/1993 |
| WO | WO2004/076621 A2 | 9/2004 |

OTHER PUBLICATIONS

Cloud et al, in Microarrays and Cancer Research, 2002, Warrington et al (Eds.), BioTechniques Press, Eaton Publishing, Westborough, MA, pp. 61-77.*
Winter G.; Griffiths A.D.; Hawkins R.E.; Hoogenboom H.R. *Making antibodies by phage display technology*, Annu Rev Immunol. 1994; 12:433, Abstract Only.
Edwin R. Hendrickson; Tina M. Hatfield Truby; Rolf D. Joerger; William R. Majarian; Richard C. Ebersole *High sensitivity multianalyte immunoassay using covalent DNA-labeled antibodies and polymerase chain reaction*, Nucleic Acids Research, 1995, vol. 23, No. 3, pp. 522-529.
Benters R.; Niemeyer C.M.; Wohrle D. *Dendrimer-activated solid supports for nucleic acid and protein microarrays*, Chembiochem Sep. 3, 2001; 2(9): 686, Abstract Only.
Maritha Mendel-Hartvig; Anil Kumar; Ulf Landegren *Ligase-mediated construction of branched DNA strands: a novel DNA joining activity catalyzed by T4 DNA ligase*, Nucleic Acids Research, 2004, vol. 32, No. 1 e2.

* cited by examiner

*Primary Examiner*—James Martinell
(74) *Attorney, Agent, or Firm*—Townsend and Townsend and Crew LLP

(57) ABSTRACT

Methods for determining the presence of an analyte in a sample are disclosed, in which a capture agent is bound to the analyte at a first epitope and a detection agent is bound at a second epitope, and in which the detection agent includes an oligonucleotide to which a labeled, complementary oligonucleotide can be hybridized.

18 Claims, 2 Drawing Sheets

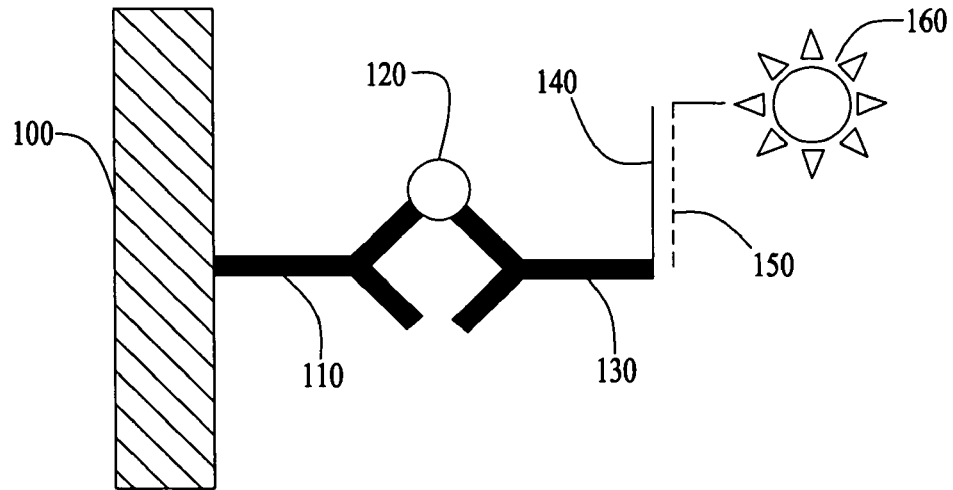
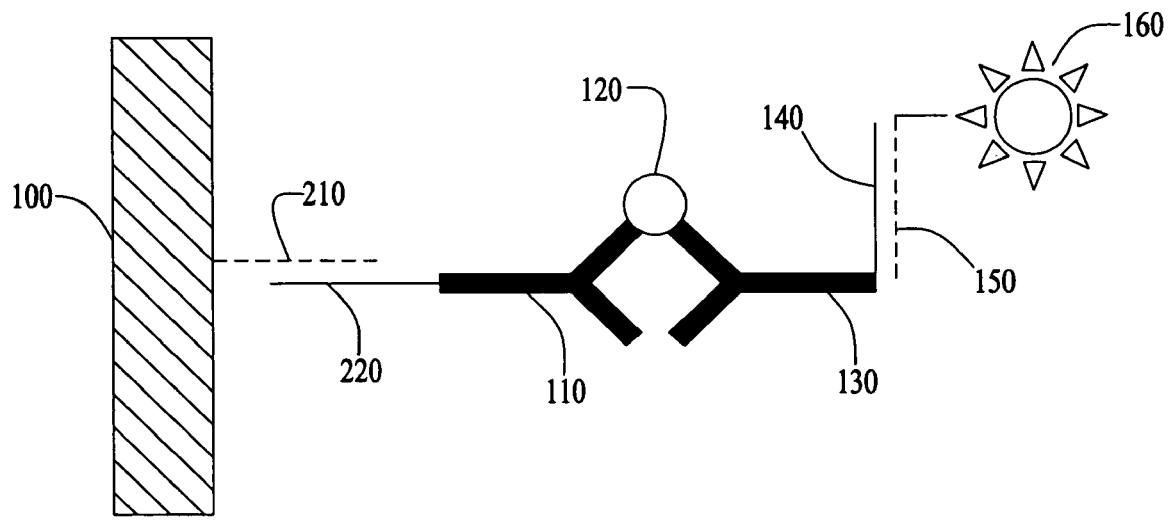

LABELED COMPLEMENTARY OLIGONUCLEOTIDES TO DETECT OLIGONUCLEOTIDE-LINKED LIGANDS

BACKGROUND

Immunoassays are an important diagnostic tool for obtaining information about the medical condition of a patient. A common immunoassay format is the sandwich assay, in which an antibody specific for a particular analyte is attached to a solid support. When the analyte is contacted with this antibody, it becomes bound to the solid support. A second, labeled antibody which is also specific for the analyte is then used to detect the binding of the analyte to the solid support.

The process of attaching a label to an antibody can, however, interfere with the antibody's ability to bind to an analyte. For example, attaching a label to an amino acid side chain within the binding site of an antibody is likely to interfere with the ability of the antibody to bind an analyte. A label can also be adversely affected in the process of coupling it to a protein. Many fluorescent dyes, for example, undergo strong quenching when they are conjugated to antibodies. The lack of ability to select discrete locations for dye attachment to proteins also greatly limits the ability to use energy transfer between fluorescent dyes to increase Stokes shift and improve assay sensitivity.

An alternative approach involves conjugating an antibody with an oligonucleotide rather than with a label. In U.S. Patent Publication No. 2004/0023271 to Kurn, for example, an oligonucleotide-conjugated antibody is contacted with a PCR primer complementary to the oligonucleotide after the antibody becomes bound to an analyte. The oligonucleotide sequence is then amplified, and the amplified sequence is detected. PCR amplification, however, requires additional time to perform cycling reactions and amplify the oligonucleotide sequence compared with standard sandwich immunoassays. The PCR amplification step, in addition, is not quantitative and introduces undesirable variation into assay results.

SUMMARY

The present system and methods overcome problems associated with attaching labels directly to antibodies and other specific binding partners used to detect analytes in sandwich assays. These problems are overcome by attaching an oligonucleotide to the antibody or other specific binding partner in place of a conventional chemical label, and then hybridizing a labeled, complementary oligonucleotide to the conjugated oligonucleotide in order to directly detect the presence of an analyte in the assay. This assay format provides additional flexibility with regard to the selection of labels to be used in a sandwich assay, as labels which might otherwise not be compatible with a particular detection agent can be incorporated into an oligonucleotide in the present system. Since dye moieties can easily be placed at discrete locations within an oligonucleotide sequence, this technology also greatly simplifies the use of well-known energy transfer dye pairs as protein labels.

The present methods for determining whether an analyte is present in a sample involve the use of: (a) a capture agent which specifically binds the analyte at a first epitope; (b) a detection agent which specifically binds the analyte at a second epitope and which also comprises a detector oligonucleotide; (c) a first labeled oligonucleotide complementary to the detector oligonucleotide; and (d) a solid support. In these methods, the sample, detection agent, and first labeled oligonucleotide are contacted with the capture agent and solid support, and the capture agent is attached to the solid support. The presence of the analyte in the sample can then be determined. Preferably, the amount of the first label bound to the solid support is determined in order to arrive at a quantitative measurement of the amount of analyte in the sample.

In one embodiment, the capture agent is attached to the solid support before the sample is contacted with the capture agent. Alternatively, the sample can be contacted with the capture agent before the capture agent is attached to the solid support. The capture agent can be attached to the solid support, for example, via an oligonucleotide on the capture agent bound to a complementary oligonucleotide bound to the solid support, and the solid support can be polypropylene, sepharose, nitrocellulose, glass, or a synthetic polymer material. The capture agent and the detection agent can be adapted to specifically bind any of a number of different analytes, such as proteins, peptides, carbohydrates, ligands, nucleic acids, lipids, steroids, metabolites, therapeutic drugs, drugs of abuse, viral antigens, bacterial antigens, disease markers, hormones, and oncogenic markers. Preferably, both the capture agent and the detection agent are antibodies.

The labels used in the present methods can include, for example, a phycobiliprotein, phycobilisome, fluorescent dye, dyed microparticle, metal sol, enzyme substrate, enzyme cofactor, enzyme inhibitor, spin label, or radioactive isotope. In one embodiment, more than one oligonucleotide can be bound to the detector oligonucleotide, in which case each oligonucleotide comprises a different label. The different labels are preferably spectrally distinct, and in one embodiment a fluorescent resonant energy transfer or other Förster-type resonance energy transfer can occur between such labels. The same oligonucleotide complementary to a sequence of a particular detector oligonucleotide can also be provided with different labels.

The detector oligonucleotide can comprise a plurality of different nucleotide sequences, preferably non-overlapping sequences, each of which is complementary to a sequence carried by a different labeled oligonucleotide. In one embodiment, the detector oligonucleotide is a branched oligonucleotide, in which a first oligonucleotide carrying a first label can be bound to the main chain of the detector oligonucleotide, and a second oligonucleotide carrying a second label can be bound to the side chain of the detector oligonucleotide.

The present methods can also be used to detect isoforms of an analyte in a sample. In this embodiment, the capture agent specifically binds to a common epitope of the analyte shared by two or more isoforms, and the detection agents bind to isoform-specific epitopes. Each detection agent comprises a detector oligonucleotide having a nucleotide sequence specific to a particular isoform, i.e. carried by detection agents specific for that isoform, as well as another nucleotide sequence common to all detection agents for the various isoforms of the analyte detected in the assay. Labeled oligonucleotides specific to each isoform-specific sequence of the detector oligonucleotides and carrying different labels are then hybridized to the detector oligonucleotides, and other labeled oligonucleotides specific to the common nucleotide sequence of the detector oligonucleotides are also hybridized to the detection agents. Prior to detecting the labeled oligonucleotides, the capture agent is attached to a solid support, which can occur either before or after contacting the capture agent with the sample. The labels carried by the oligonucleotides hybridized to the isoform-specific and common nucleotide sequences of the detector oligonucleotides are then detected in order to determine whether any isoforms of the analyte are present in the sample. The amount of each isoform in the sample, as well as the total amount of the analyte in the sample, can also be determined.

In a further aspect, kits for conducting an assay for an analyte can be provided. Such kits include a capture agent which specifically binds the analyte at a first epitope; a detection agent comprising a detector oligonucleotide, the detection agent specifically binding the analyte at a second epitope; a first labeled oligonucleotide; and a second labeled oligonucleotide. The capture agent is adapted to be bound to a solid support, which can be a planar surface, a fiber, a capillary, a particle, or other support known to the art. The detector oligonucleotide, which can be a branched oligonucleotide, comprises at least two nucleotide sequences. The first labeled oligonucleotide is complementary one sequence of the detector oligonucleotide, while the second labeled oligonucleotide is complementary to a second (preferably non-overlapping) nucleotide sequence of the detector oligonucleotide, and the two labeled oligonucleotides comprise different labels, i.e. labels which are spectrally distinct or otherwise distinguishable. Any of the labels described herein can be incorporated into the labeled oligonucleotides.

Other kits for conducting an assay for isoforms of an analyte are also provided. Such kits include a capture agent which specifically binds both a first isoform and a second isoform of the analyte, preferably at an epitope common to both isoforms; a first detection agent which specifically binds the first isoform of the analyte at an epitope specific to that isoform which is different from the epitope bound by the capture agent, the first detection agent having a first detector oligonucleotide; a second detection agent which specifically binds the second isoform of the analyte at an epitope specific to that isoform which is different from the epitope bound by the capture agent, the second detection agent having a second detector oligonucleotide; a first labeled oligonucleotide complementary to the first detector oligonucleotide; and a second labeled oligonucleotide complementary to the second detector oligonucleotide. The first and second detector oligonucleotides can also comprise a nucleotide sequence common to both the first and second detector oligonucleotides, and a third labeled oligonucleotide carrying a label different from that carried by the first and second labeled oligonucleotides can be included in the present kits, in order to detect all isoforms of an analyte. Isoforms that can be detected with the present kits include, e.g., isoforms of PSA.

DRAWINGS

These and other features, aspects and advantages of the present invention will become better understood with regard to the following description, appended claims, and accompanying figures where:

FIG. 1 is an illustration of the binding of an analyte in one embodiment of the present system and methods.

FIG. 2 is an illustration of the binding of an analyte in another embodiment of the present system and methods.

Figure 3:
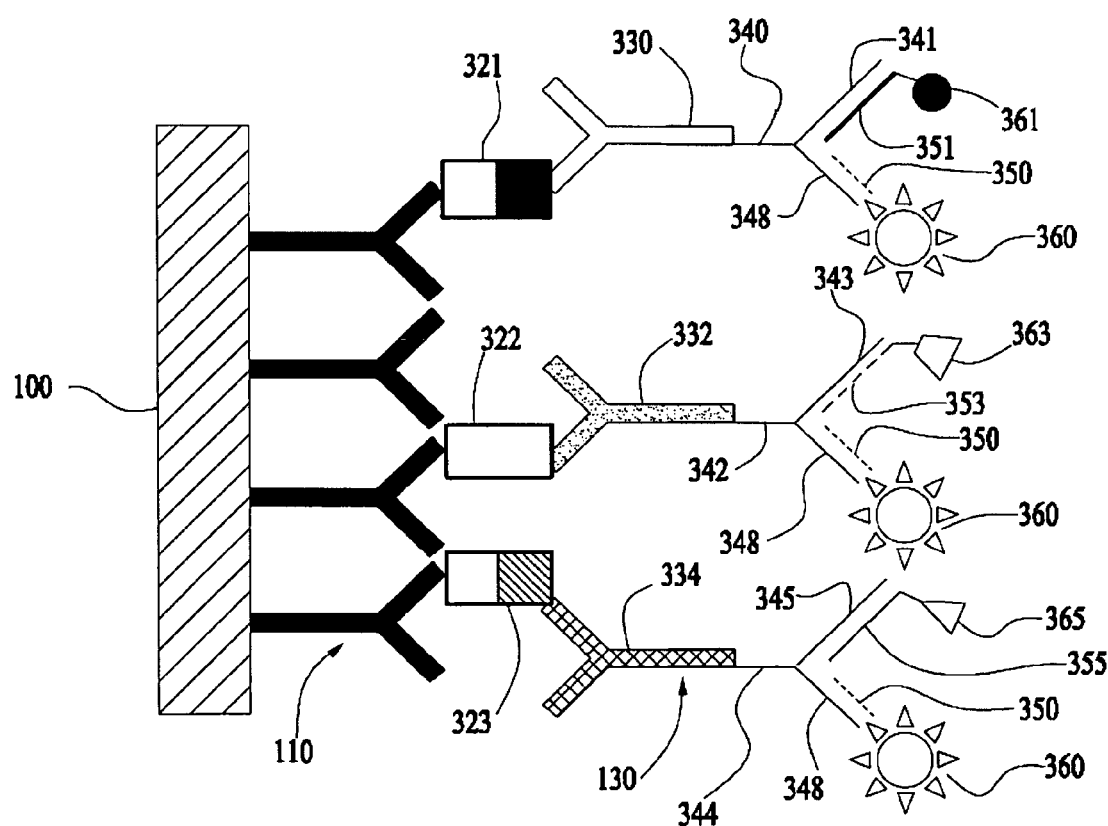
FIG. 3 is an illustration of the binding of isoforms of an analyte in another embodiment of the present system and methods, in which the detector oligonucleotide is a branched oligonucleotide.

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by their intended use.

DESCRIPTION

Definitions

As used herein, the following terms and variations thereof have the meanings given below, unless a different meaning is clearly intended by the context in which such term is used.

"Analyte" refers to a molecule, compound, or other component in a sample. Analytes include but are not limited to peptides, proteins, polynucleotides, organic molecules, sugars and other carbohydrates, and lipids. For example, an analyte can be a vitamin, hormone, drug, virus or bacterium. An analytes can also comprise a portion of another molecule.

"Antibody" refers to an immunoglobulin protein or to a fragment or derivative thereof which specifically binds to an analyte. Antibodies include various classes and isotypes of immunoglobulins, such as IgA, IgD, IgE, IgG1, IgG2a, IgG2b, IgG3, and IgM. Antibody fragments include molecules such as Fab, scFv, F(ab')$_2$, and Fab' molecules. Antibody derivatives include antibodies or fragments thereof having additions or substitutions, such as chimeric antibodies. Antibodies can be derived from human or animal sources, from hybridomas, through recombinant methods, or in any other way known to the art.

"Aptamer" refers to a single-stranded polynucleotide or polypeptide specific binding partner. Aptamers are generally short polymers (e.g., 20-100-mers) which fold into stable three-dimensional structures that have highly specific and selective binding activities.

"Array" refers to a two-dimensional arrangement of molecules on a surface of a solid support. The surface can be planar or curved.

"Capture agent" refers to a specific binding partner for an analyte which is attached or is adapted to be attached to a solid support. A capture agent specifically binds an analyte at an epitope which is spatially distinct from the epitope bound by a detection agent so that the binding of an analyte by a capture agent and a detection agent is not sterically hindered to an extent that would interfere with an assay. Capture agents can be either reversibly or irreversibly attached to a solid support.

"Complementary," with respect to a polynucleotide, refers to a polynucleotide molecule that is able hybridize to another polynucleotide under the conditions of an assay performed according to the present methods. Preferably, non-specific hybridization of complementary polynucleotides occurs at a frequency of less than about 5%, and more preferably less than about 0.1%. Non-specific hybridization includes Watson-Crick base pair interactions other than those between adenine and thymine or uracil, or between cytosine and guanine.

"Detection agent" refers to a molecule comprising a specific binding partner for an analyte and which further comprises a detector oligonucleotide.

"Detector oligonucleotide" refers to an oligonucleotide attached or otherwise linked to the specific binding partner of a detection agent.

"Epitope" refers to a localized region or regions on the surface of an analyte to which a capture agent or detection agent binds.

"Hybridize" refers to the formation of a double-stranded nucleic acid structure between at least two complementary polynucleotides. Such binding generally occurs via hydrogen bond interactions, such as Watson-Crick base pair interactions.

"Isoforms" refer to different polypeptide molecules derived from polynucleotides having the same nucleic acid sequence or having homologous sequences. Isoforms typically have significant amino acid sequence homology, and differences between isoforms are frequently due to alternate splicing of a polynucleotide, to the existence of alternate start codons in such polynucleotides, or to post-translational modification such as glycosylation and phosphorylation. For example, transforming factor beta (TGF-B) exists in three isoforms, TGF-B1, TGF-B2, and TGF-B3. Free prostate specific antigen (PSA) likewise occurs in several isoforms, including f-PSA, PSA-ACT, PSA-MG, pPSA, BPSA, and iPSA.

"Label" refers to a moiety that provides a detectable signal, which can be attached to or incorporated into a binding partner, either directly or indirectly. Examples of labels include but are not limited to fluorescent dyes, dyed microparticles, fluorescent proteins, fluorescent nanocrystals (quantum dots), metal sols, enzymes, enzyme substrates, enzyme cofactors, enzyme inhibitors, spin labels, and radioactive isotopes. A label is typically detected by a detector, which can be part of an analytical instrument.

"Labeled oligonucleotide" refers to an oligonucleotide which is complementary to a detector oligonucleotide and which includes a label.

"Nucleotide sequence" refers to a chain of consecutive nucleotides in a polynucleotide molecule.

"Oligonucleotide" refers to a linear or branched polynucleotide molecule that comprises between about 5 and 200 nucleotides or analogs thereof.

"Peptide" refers to an amino acid sequence comprising 50 or fewer amino acids, while "protein" refers to an amino acid sequence of greater than 50 amino acids.

"Polynucleotide" refers to a molecule comprising two or more nucleotides or analogs thereof, and includes DNA and RNA. Nucleotide analogs are nucleotides which have modified base and/or sugar moieties or which include substitutions, such as peptide nucleic acids in which the sugar phosphate backbone of a natural nucleic acid is replaced by a synthetic peptide backbone. The nucleic acids of a polynucleotide are usually linked by phosphodiester bonds but can also be linked via phosphorothioate, phosphoranilidate, or phosphoramidate binding.

"Solid support" refers to a material which is insoluble (i.e., not easily dissolved) in the presence of the reagents used in the present methods. Solid supports include particles, fibers, and planar surfaces and are generally made from materials which are only poorly soluble in water such as sepharose, nitrocellulose, glass, and a number of synthetic polymers.

"Specific binding" or "specifically bind," with respect to the interaction between an analyte and a specific binding partner, refers to the attachment of the specific binding partner to the analyte and not to other components of a sample. A specific binding partner can in some cases bind a particular group or class of molecules and still be regarded as specifically binding such molecules. For example, the capture agent can be directed against the Fc region of a class of antibodies and thereby specifically bind a number of different antibodies of that particular class, or can bind to different isoforms of an analyte. The binding of an analyte by a specific binding partner can be reversible, i.e. the analyte can be detached from the specific binding partner without structurally altering the analyte and/or the specific binding partner, or can be irreversible (such as the binding between biotin and avidin).

"Specific binding partner" refers to a molecule capable of specifically binding an analyte, other than through Watson-Crick base pair interactions. A specific binding partner can be any of a number of different types of molecules, including an antibody or other protein, peptide, polysaccharide, lipid, or aptamer.

"Spectrally distinct," in reference to a plurality of fluorescent labels or other optically detected labels, means that the optical absorption or emission bands of the labels are sufficiently distinct, i.e. sufficiently non-overlapping, that molecules to which the respective labels are attached can be distinguished on the basis of the optical signals generated by the respective labels using a photodetection system, such as a spectrophotometer or fluorometer.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Assay Components

Specific Binding Partners

A number of different types of specific binding partners can be used in the present system and methods, depending on the analyte to be detected. In one embodiment, the specific binding partner is an antibody. Antibodies used as capture agents or detection agents to bind a particular analyte are preferably monoclonal, and thus are directed against a single epitope of an analyte. Monoclonal antibodies can be prepared using techniques known to the art, and are typically prepared through the creation of a hybridoma using a B-cell line that produces an antibody with desired binding characteristics. Antibodies directed against a single epitope can also be generated in other ways, such as through recombinant methods.

In some embodiments, polyclonal antibodies can be used as specific binding partners in the present system and methods. For example, a capture agent can comprise polyclonal antibodies raised against epitopes of an analyte which are different from the epitope or epitopes recognized by a detection agent used to detect the analyte. Polyclonal antibodies can be prepared in ways known to the art, such as by the immunizing a host and collecting plasma or serum from that host.

Antibody fragments which retain their specific binding characteristics can also be used as specific binding partners in the present system and methods, including fragments lacking the Fc portion of an antibody, e.g., Fab, Fab' and F(ab')$_2$ fragments. Fab and F(ab')$_2$ fragments can be produced by methods known to the art, e.g. by cleaving a monoclonal antibody with proteolytic enzymes such as papain and pepsin. Fab' fragments can be produced by reductive cleavage of F(ab')$_2$ fragments with agents such as dithiothreitol or mercaptoethanol. Antibody fragments can alternatively be produced using recombinant methods, such as through the use of a phage display library [see, e.g., Winter et al., Ann. Rev. Immunol., 12: 433-455 (1994)].

Antibody derivatives such as single chain antibodies or fragments thereof can also be used. Single chain Fv (scFv) antibodies incorporate an entire antibody binding region in one single polypeptide chain. Such antibodies are obtained either recombinantly or by reductive cleavage of the disulfide bonds connecting the heavy chain components of an intact antibody. Other antibody derivatives which can be used include miniantibodies, bispecific antibodies (diabodies), multimers of antibodies or antibody derivatives, and peptides which include sequences from antibody binding regions, for example from one or several CDR's (complement determining regions) of an antibody, preferably including the CDR3 region.

Specific binding partners other than antibodies or antibody fragments or derivatives can also be used in the present system and methods. For example, aptamers can be used as specific binding partners. Specific binding partner pairs that can be used include receptor-ligand, enzyme-substrate, enzyme-inhibitor, and enzyme-cofactor pairs. Specific examples of such specific binding partner pairs include carbohydrate and lectin, biotin and avidin or streptavidin, folic acid and folate binding protein, vitamin B12 and intrinsic factor, Protein A and immunoglobulin, and Protein G and immunoglobulin. Also included are specific binding pairs that form a covalent bond with each other.

Oligonucleotides for Detection

Oligonucleotides can be used in several aspects of the present system and methods. In one aspect, oligonucleotides are used to label a detection agent bound to an analyte. The detection agent of the present system comprises an oligonucleotide, the detector oligonucleotide, and when a complementary, labeled oligonucleotide is hybridized to this detector oligonucleotide, the label moiety of the labeled oligonucleotide becomes associated with the detector oligonucleotide. The detection agent can then be detected and preferably measured using suitable equipment.

The detector and labeled oligonucleotides can be either straight chain or branched oligonucleotides. Preferably, such oligonucleotides have a length of between about 5 and 100 nucleotides, and more preferably comprise at least about 20-30 nucleotides in order to assure specific hybridization between complementary oligonucleotides. In general, it is preferred that oligonucleotide pairs be completely complementary, i.e. that each nucleotide of one oligonucleotide is bonded to a nucleotide of the other oligonucleotide under the conditions of an assay, over at least a portion of their respective sequences. These complementary portions of the sequences should comprise at least about 20 bases, and more preferably at least about 30 bases.

In one embodiment, branched oligonucleotides can be used as detector oligonucleotides in the present system. A branched oligonucleotide comprises at least one nucleotide sequence attached to an internal nucleotide or other moiety of a polynucleotide molecule as a side chain. For example, as shown in FIG. 3, detector oligonucleotide 340 comprises side chains 341 and 348 which are complementary, respectively, to labeled oligonucleotides 351 and 350. Such a branched detector oligonucleotide can be constructed, for example, by including an internal 3' hydroxyribonucleotide residue in an oligonucleotide which can be joined to the 5' end of another oligonucleotide using T4 DNA ligase [see, e.g., Mendel-Hartvig, M, et al., Nucleic Acids Research, Vol. 32, No. 1, e2 (1994)]. Alternatively, a branched detector oligonucleotide can comprise a 3'-3'-linked branched oligonucleotide having a pentaerythritol linker and can be prepared using a DNA synthesizer. Branched oligonucleotides, having a fork-like structure, present multiple binding sites for oligonucleotides. For polynucleotide chains longer than 100 nucleotides, the use of branched oligonucleotides allows chains to be produced with a lower error rate, as multiple smaller oligonucleotides can be combined in such branched structures.

One advantage of binding labeled oligonucleotides to the detection agent in the present system and methods is that this allows one antibody conjugate (or other detection agent) to be readily labeled by many different kinds of labels. This is accomplished by preparing oligonucleotides that are complementary to the same sequence of a detector oligonucleotide (i.e., the oligonucleotide conjugated to the detection agent) and then labeling such complementary oligonucleotides with different labels. Such differently labeled complementary oligonucleotides can be hybridized to a detection agent using the same set of reaction conditions, so that a set of reaction conditions optimized for a particular detection agent and a particular labeled, complementary oligonucleotide can be used with different detection systems, without having to invest the time and resources to optimize reaction conditions for a different labeled oligonucleotide. This makes the present system particularly suitable for multiparameter detection systems.

Another advantage of the present system is that dyes that show strong quenching when attached directly to proteins (i.e., cyanine dyes) can be used for labeling, since the labels used in the present system and methods are attached to an oligonucleotide. For example, multiple dyes can be attached to defined positions on a labeled oligonucleotide, thereby minimizing the quenching normally found when such dyes are incorporated at high levels of substitution into antibodies and other proteins. Moreover, multiple dyes can be incorporated at specific sites on a labeled oligonucleotide to form efficient energy transfer complexes, providing a large Stoke shift that effectively reduces assay background. In addition, dyes that are normally too hydrophobic for conjugation to a protein or other molecule in aqueous solution can be incorporated into a labeled oligonucleotide by means of solid phase synthesis in an organic phase, and the freely soluble labeled oligonucleotide can then subsequently be used in the present system and methods.

In one preferred embodiment, a plurality of different labels are incorporated into different oligonucleotides. For example, when assaying for isoforms of a particular analyte, one particular label can be incorporated into a labeled oligonucleotide used to detect all isoforms of the analyte, so that when this label is detected, a total amount of all isoforms of this species can be calculated. The labeled oligonucleotides in isoform assays generally also include a different label and sequence for each individual isoform of an analyte so that the assay can distinguish the presence and/or quantity of the different isoforms of the analyte. When multiple labels are used in an assay in the same labeled oligonucleotide or otherwise are bound to the same detection agent, they should be selected so that they do not interfere with one another when being detected.

Oligonucleotides for Capture

In another aspect of the present system and methods, an oligonucleotide can be used to attach a capture agent to a solid support (see, e.g., U.S. Pat. No. 5,648,213). In this aspect of the invention, an oligonucleotide is attached to a capture agent and a complementary oligonucleotide is attached to a solid support. When the capture agent is then contacted with the solid support under conditions which allow hybridization between the solid support-bound oligonucleotide and the capture agent oligonucleotide, these oligonucleotides will hybridize and the capture agent will thereby be reversibly bound to the solid support.

Oligonucleotides can be attached to a solid support in ways known to the art. For example, polypropylene microtiter plates can be derivatized with amine groups as described in U.S. Pat. No. 5,112,736 and then linked to oligonucleotides with 1,1'-carbonylditriazole, as described in U.S. Patent Publication No. 20030092062.

Another method of covalently attaching an oligonucleotide to a support is silanization. For example, a glass surface can be silanized with (3-aminopropyl) triethoxysilane (APTES) to generate a surface containing amino groups. The terminal amino groups on the silanised surface can then be reacted with 1,4-diphenylene diisothiocyanate (DPC) to convert the amino groups to phenyleneisothiocyanate groups. These in turn are reacted with 5'-amino modified oligonucleotides to yield surface bound oligonucleotides (see, e.g., U.S. Pat. No. 5,622,826). Oligonucleotides can also be activated with other agents, such as a carbodiimide, in order to attach them to a solid support (see, e.g., U.S. Pat. No. 6,146,833). Alternatively, an oligonucleotide that has been biotinylated, such as with a biotin phosphoramidite (available, e.g., from Applied Biosystems, Foster City, Calif.), to create a 5'-biotinylated oligonucleotide can be reacted with an avidin moiety attached to a solid support in order to specifically bind the oligonucleotide to the support.

Labels

A wide variety of labels can be used in the present system. Labels are attached to, incorporated into, or otherwise associated with the labeled oligonucleotides which are complementary to the detector oligonucleotides of the present system. Examples of labels include fluorescent moieties, phosphorescent moieties, chemiluminescent moieties, colored particles, enzymes, enzyme substrates, enzyme cofactors, enzyme inhibitors, radioactive isotopes, chromogens, dyes, metal sols, chelating compounds, mass labels, and spin labels. Labels can be detected based on fluorescence, luminescence, radioactivity, enzymatic activity, or other property.

Light-emitting compounds used as labels include fluorescent labels such as fluorescent dyes, fluorescent proteins, and fluorescent nanocrystals. Fluorescent dyes include, for example, fluorescein, rhodamine, coumarin, and derivatives thereof (available, for example from Sigma-Aldrich Corporation, St. Louis, Mo.) and Alexa Fluor dyes (available from Molecular Probes, Inc., Eugene, Oreg.). Fluorescent proteins include phycobiliproteins (such as allophycocyanin, phycocyanin, and phycoerythrin), phycobilisomes, green fluorescent protein, red fluorescent protein, and various derivatives of such proteins. Other fluorescent compounds which can be used as labels include nanocrystals, also referred to as quantum dots.

In one embodiment, fluorescent labels can comprise an acceptor-donor pair of molecules which interact via Förster resonance energy transfer (FRET). For example, one member of such a FRET pair can be incorporated into the detector oligonucleotide, and the other member can be incorporated into the labeled oligonucleotide, so that hybridization of the labeled oligonucleotide to the detector oligonucleotide results in a detectable FRET interaction. This allows detection of the hybridization of the labeled oligonucleotide without having to perform a wash step to remove unhybridized labeled oligonucleotide molecules. The acceptor-donor pair of molecules in this embodiment can both be fluorescent dyes, for example. Alternatively, one member of the FRET pair can be a luminescent moiety or a quencher. In another embodiment, a single labeled oligonucleotide sequence can contain two or more fluorescent moieties positioned at discrete locations for efficient FRET, producing a larger Stokes shift than would be observed from individual dyes.

Chemiluminescent labels for use in the present system include acridinium esters, luminol and its derivatives, dioxetane derivatives, aequorin and luciferins.

Electroluminescent labels, such as ruthenium chelates and their derivatives or agents that possess nitroxide moieties, can also be used when a high degree of sensitivity is needed. Other labels which produce optical signals include, for example, dyed microparticles which incorporate dyes internally, such as OptiBind polystyrene and OptiLink carboxylate-modified microparticles (available from Seradyn Inc., Indianapolis, Ind.).

Enzymes suitable for use as labels include, but are not limited to, hydrolases, lyases, oxido-reductases, transferases, isomerases ligases, peroxidase, phosphatases, esterases and glycosidases. Specific examples include luciferase, glucose oxidase, alkaline phosphatase, lipases, beta-galactosidase, horseradish peroxidase and porcine liver esterase. In embodiments where enzymes serve as labels, a substrate/enzyme reaction forms a product which results in a detectable signal, typically a change in color, in which case a chromogenic substrate of the enzyme must be added to the reaction mixture in the present methods. For example, 3,3' diaminobenzidine (DAB) can be contacted with horseradish peroxidase in order to produce an optical signal. Substrate systems are also available that produce insoluble fluorescent products, for example the ELF substrate system (available from Invitrogen Corporation, Carlsbad, Calif.) for alkaline phosphatase. A luminescent signal can also be produced enzymatically, such as with luciferase.

Spin labels can also be used as labels in the present system and methods. Spin labels are molecules which contain an atom or a group of atoms exhibiting an unpaired electron spin that can be detected by electron spin resonance spectroscopy, such as transition metal ions and free radicals. For example, the spin label can be 1-oxyl-2,2,5,5-tetramethylpyrroline-3-methyl)-methane thiosulfonate, which contains a paramagnetic nitroxide side chain. Radioactive labels can also be used in the present assays, although they are less preferred due to the difficulty and expense of disposing of materials containing such labels. Nucleotides can be labeled, for example, on their 5' ends using T4 polynucleotide kinase and $^{32}P$ gamma-labeled ATP.

Labels can be attached to oligonucleotides in ways known to the art. For example, oligonucleotides incorporating a primary amine can be conjugated to a variety of labels. A reagent such as TFA Aminolink phosphoramidite (available from Applied Biosystems, Foster City, Calif.) can establish such an amino group at the 5'-end of an oligonucleotide during nucleic acid synthesis. Labels can also be incorporated into an oligonucleotides at the 3' end of the oligonucleotide, such as through the use of terminal deoxynucleotidyl transferase (TdT). Alternatively, labels can be directly incorporated into the sequence of the oligonucleotide during synthesis using dye-phosphoramidites. This has the advantage of allowing labels which are poorly soluble in aqueous solutions to be incorporated into a labeled oligonucleotide. In order to increase the sensitivity of the present assays, more than one label moiety can be incorporated into a labeled oligonucleotide.

Labels can be detected with detectors, such as microwell plate readers, flow cytometers, spectrophotometers, fluorometers, and mass spectrometers. The particular detector to be used will depend on the label and on the solid support used in a particular assay, as is known to those of skill in the art.

Solid Supports

The solid support can be made from any material to which a capture agent can be bound which doesn't interfere with conducting an assay according to the present methods, and which is insoluble in the presence of reagents used in the present methods. Suitable materials include nitrocellulose, glass, and a number of synthetic polymers, including nylon, polyvinylidene fluoride (PVDF), polystyrene, polypropylene, polycarbonate, polyglycidylmethacrylate, polyacrylamide, polyamide, and polyvinylchloride. Particle supports can be made, e.g., of sepharose.

In some embodiments, the solid support comprises a planar surface to which capture agents are attached in an array. For example, the solid support can be a microwell plate, well, membrane, waveguide, or other relatively planar surface. In one preferred embodiment, different oligonucleotides are attached to different predefined regions of a substantially planar surface, such as the surface of a well of an A.sup.2 Plate (available from Beckman Coulter, Inc., Fullerton, Calif.), and capture agents comprising complementary oligonucleotides are hybridized to them, thereby attaching the capture agents to the surface.

In other embodiments, the solid support can comprise a particle. Particle supports can range in size of from about 50 nm to about 500 µm, and can comprise particles such as Fractogel polyvinylidene methacrylate particles (available from Merck KgaA, Darmstadt, Germany), sepharose particles (available from Amersham Biosciences Corp., Piscataway, N.J.), magnetic particles, paramagnetic particles, and latex particles.

Planar and fiber optic waveguides can also be used as solid supports. Such supports propagate light within an optical waveguide by internal reflection, with an evanescent wave penetrating a fraction of a wavelength into an aqueous phase covering the support. The evanescent wave optically interacts with molecules, such as fluorescent moieties, located on the waveguide surface. Such labels can be excited by the evanescent wave and thereby be detected without the necessity of washing away unbound labeled oligonucleotide.

Capture Agents and Detection Agents

The capture agent used in the present system and methods, which comprises a specific binding partner, can be attached to a solid support in ways known to the art. In one embodiment, the capture agent can be directly and irreversibly attached to the solid support, e.g. through adsorption, covalent bonding, or through a biotin-avidin or similar linkage. In a preferred embodiment, the capture agent is reversibly bound to a solid support. For example, the capture agent can first be conjugated to an oligonucleotide, and can then be bound to a solid support via a complementary oligonucleotide which is attached to the support. This approach has several advantages, including the ability to specifically bind the capture agent to a particular location on a solid support and the ability to use a single type of support with a wide variety of capture agents (see, e.g., U.S. Pat. No. 5,648,213).

An oligonucleotide can be attached to a capture agent or to a detection agent in ways known to the art. For example, an oligonucleotide having an attached linker, such as a derivatized PEG polymer or oligomer, can be conjugated to protein or lipid specific binding partners. A heterobifunctional PEG oligomer for use herein can have an NHS ester at one terminus and a protected hydrazide at the other terminus.

When the capture agent or detection agent is an antibody or other protein or peptide, it can be bound to an oligonucleotide with a homobifunctional agent, i.e., one which bonds to both the antibody and oligonucleotide, such as 1,4-phenylene diisothiocyanate and disuccinimidylglutarate (DSG). For example, the oligonucleotide can be provided with a terminal primary aliphatic amine by employing, in a coupling step, a 5' aminohexyl phosphate linker such as the reagent Aminolink2 (available from Applied Biosystems, Foster City, Calif.), a phosphoramidite coupling reagent having a trifluoroacetyl-protected amino side chain. The oligonucleotide can then be linked to reactive moieties on the antibody, such as the amine groups.

In other embodiments, a capture agent (and/or a detection agent) can be bound to an oligonucleotide in a two step process, whereby the capture agent and oligonucleotide are separately reacted or otherwise prepared for attachment to each other. For example, an avidin moiety can be attached to an oligonucleotide and a biotin moiety can be attached to a capture agent. The oligonucleotide will then become bound to the capture agent when the two components are brought into contact.

Alternatively, an oligonucleotide can be first reacted with a heterobifunctional linker comprising a first group reactive with an amino group of the oligonucleotide, after which a second group of the linker can be reacted with a thiol group of a polypeptide comprising the capture or detection agent, such as an antibody (as described in U.S. Patent Publication No. 20030092901). The linker can be, for example, SMCC(N-succinimidyl-4-(maleimi-domethyl cyclohexane)-1-carboxylate) or a more water soluble analog such as sulfo-SMCC (available from Pierce Biotechnology, Rockford, Ill.). These reagents contain, at one terminus, an NHS ester group, which is displaced by an amine on the protein capture agent or oligonucleotide, and at the other terminus, a maleimide group.

In one embodiment, an amine group on an antibody is reacted with SMCC to produce a maleimide derivative. An active amine on an oligonucleotide is reacted with 2-aminothiolane (Traut's reagent) to produce a terminal thiol group attached to the oligonucleotide. Reaction of the activated antibody and oligonucleotide components then produces the conjugate. In a variation on this procedure, the thiolating reagent SATA (N-succinimidyl-S-acetylthioacetate) can be used to produce a protected thiol functionality on either component.

Assay Methods

The present methods relate to sandwich-type assays in which a specific binding partner is bound to an analyte, and an oligonucleotide conjugated to the specific binding partner is directly detected by means of a complementary labeled oligonucleotide. One embodiment of the present method is illustrated in FIG. 1. FIG. 1 depicts a capture agent comprising an antibody 110 directly attached to a solid phase 100. Bound to the capture antibody 110 is an analyte 120 from a sample. A second analyte-specific antibody 130 conjugated with a detector oligonucleotide 140 (together forming the detection agent) are bound to a different epitope of the analyte 120. A detectable label 160 is attached to a complementary oligonucleotide 150, which is hybridized to the detector oligonucleotide 140 of the detection agent. In this embodiment, the capture antibody 110 is attached to the solid support 100 before the sample is contacted with the capture antibody 110.

As shown in FIG. 2, the capture antibody 110 can also be bound to the solid support 100 via oligonucleotides 210 and 220. In this embodiment, an oligonucleotide 210 is bound to the solid support 100, and another oligonucleotide 220 bound the capture antibody 110 comprises a nucleotide sequence complementary to a sequence of the support oligonucleotide 210. The capture antibody 110 becomes bound to the solid support 100 when these two components are contacted under conditions which allow the oligonucleotides 210 and 220 to hybridize.

In the embodiment illustrated in FIG. 2, the present assay comprises a homogeneous format in which all of the assay components (e.g., the sample, a capture agent, a detection agent, and a complementary labeled oligonucleotide) can be introduced in the solution phase to form complexes comprising an analyte and a capture and detection agent, i.e. a sample is contacted with the capture agent (and/or the detection agent) before the capture agent is attached to the solid support. The kinetics of forming a complex via a homogeneous reaction among the capture agent, detection agent, complementary labeled oligonucleotide, and an analyte in solution are significantly faster than would be the case with a heterogeneous reaction between solution-phase materials and a solid material (e.g., a capture reagent bound to a solid support, as illustrated in FIG. 1). A reaction mixture containing the solution phase complex can then be contacted with a support to which, e.g., an oligonucleotide is attached so that a complementary oligonucleotide attached to the capture agent hybridizes with the support oligonucleotide, thereby effectively harvesting the complex onto the support. Any material not bound to the complex remains in the solution phase and can readily be separated from the complex and the solid support.

The detection method used in the present system and methods to determine the presence of an analyte in a sample or to determine the quantity of the analyte in the sample depends on the labels used. For example, when the label is a fluorescent dye such as fluorescein or rhodamine, the method of detecting the label can be laser scanning confocal microscopy (LSCM), wide-field fluorescence microscopy, or a CCD camera. When the label is an enzyme and a signal is produced with a chromogenic substance, such as horse-radish peroxidase with 3,3' diaminobenzidine (DAB), a spectrophotometer can be used for detection. Methods known to the art for detecting other labels can likewise be employed.

Assay Conditions

In the present methods, a complex is formed among an analyte, a capture agent, a detection agent, and one or more sets of oligonucleotides. The formation of this complex in solution can be effected under a wide range of conditions, depending on the analyte, capture agent, detection agent, and oligonucleotides used. In general, complex formation occurs more rapidly for a given concentration of analyte at higher concentrations of capture agent and/or detection agent. An excess of the capture and detection agents is preferably used, and preferably at least a two-fold excess of capture and/or detection agent is used relative to the amount (or expected amount) of the analyte in a sample.

Complex formation can occur over a wide range of temperatures, limited by the denaturing temperature of the capture agent, detection agent, and analyte. Preferably, the complex formation is carried out at a temperature in the range of about 15° C. to about 70° C., and most preferably (for purposes of convenience) at room temperature. The pH can also be varied over a broad range, with the limiting factor being the pH at which the reactants become denatured. The pH is normally in the range of about 2 to about 11, preferably about 4 to about 10, and most preferably close to 7. In addition, various materials, such as fetal calf serum proteins, can be used to minimize non-specific interactions.

In the present methods, the reaction conditions used to bind the capture agent, detection agent, and analyte should also allow the hybridization of the detector oligonucleotide attached to the detection agent with a complementary labeled oligonucleotide. Preferably, the capture agent is also attached to a solid support via complementary oligonucleotides, as described above. Appropriate conditions for the formation of a duplex between such complementary oligonucleotides can be determined by those of skill in the art. Appropriate temperatures for performing the present methods can also be determined by those of skill in the art. Preferably, a temperature less than the melting temperature (Tm, the temperature at which 50% of a pair of complementary oligonucleotides form duplexes) is used.

Assay conditions for the present methods are preferably selected such that the detector oligonucleotide hybridizes only to its specific complementary labeled oligonucleotide. While the labeled oligonucleotide may non-specifically hybridize to other oligonucleotides at a relatively low rate in the present methods, assay conditions are preferably selected so that such cross-hybridization occurs at a rate of less than 5%, more preferably less than about 0.1%, and even more preferably at a rate of less than about 0.01%, in order to minimize interference with assay results. Preferred assay conditions include a pH of about 7, an ionic strength of between about 50 mM and 500 mM, and a temperature between about 2° C. and 45° C. Up to 25% v/v organic compounds, such as glycerol or formamide, can be included in an assay solution in order to improve the fidelity of hybridization.

In a preferred embodiment, in which the capture agent is attached to the solid support by means of complementary oligonucleotides, the capture agent can be released from the solid support and the support can be used in another assay with the same or different capture agent. Bound capture agents can be released from the support using appropriate dissociation conditions. Deionized water or a concentrated solution of urea (e.g., 7M) or formamide (e.g., 30%-60% in water) can suitably be used. Alternatively, a capture agent can be retained on the solid support, and the analyte and detection agent can be removed in order to reuse the capture agent attached to the support.

Isoform Detection

Isoforms in a sample can advantageously be detected with the present methods and system. When detecting isoforms in a sample, a capture agent capable of specifically binding all of the isoforms can be used together with detection agents specific for each isoform. Each of such detection agents will comprise a detector oligonucleotide having a different nucleotide sequence, so that each detection agent can be hybridized with a labeled oligonucleotide carrying a different label.

In one embodiment, illustrated in FIG. 3, the detector oligonucleotide of a detection agent can be hybridized with two different labeled oligonucleotides when detecting isoforms. One of the labeled oligonucleotides 350 can comprise a sequence complementary to a sequence 348 carried by all of the detector oligonucleotides 340, 342, 344 used in the assay, so that detection of the label 360 of such labeled oligonucleotides 350 can indicate the presence or quantity of all isoforms 321, 322, 323 of a specific analyte in the sample. Each detection antibody used in this assay is specific for a particular isoform, and each antibody includes an oligonucleotide having a different sequence, so that labeled oligonucleotides 351, 353, and 355 bound to antibodies 330, 332, 334 and complementary to oligonucleotide sequences 341, 343, 345, respectively, can be detected to determine the presence or quantity of a specific isoform of an analyte in the sample. The labeled oligonucleotides 351, 353, and 355 each carry a different label 361, 363, 365, respectively. The labels used to identify each isoform should be different from each other and also different from the label used to identify all isoforms in the sample.

As illustrated in FIG. 3, isoforms can be detected through the use of detector oligonucleotides comprising branched oligonucleotides, though unbranched structures can also be used. One branch of each of the branched oligonucleotides 340, 342, 344, for example, can comprise a sequence 348 common to detector oligonucleotides 350 carried by all of the isoform-specific detection antibodies 330, 332, 334. Another branch of each of the branched oligonucleotides 340, 342, 344 can comprise one of the sequence 341, 343, or 345 specific to a particular isoform 321, 322, 323, respectively, of the analyte, and a complementary oligonucleotide 351, 353, or 355, respectively, can be bound to that sequence in order to detect the amount of the analyte corresponding to that isoform in a sample.

In one example, isoforms of free prostate specific antigen (PSA) can be detected with the present system and methods. PSA occurs in several isoforms, including pPSA, BPSA, and iPSA, and determining the relative frequency of these isoforms can be useful in distinguishing benign prostrate hypertrophy from prostate cancer. The present methods permit such determinations to be made within a single test area, along with quantitating total free PSA, for a particular sample. Multiple oligonucleotides can also be printed in spatially distinct regions within a test area in order to permit simultaneous characterization of the isoform distribution of a variety of different analytes using the present methods.

EXAMPLES

Example 1

Preparation of Oligonucleotide-Bound Plates

Polypropylene plates were aminated by placing them in a plasma chamber and aminating them with ammonia gas using a Plasma Science, Model 0150E Animator (Plasma Science, Airco Coating Technology, 2700 Maxwell Way, Fairfield, Calif. 94533). The plates were subjected to the following conditions:

Step I: Ammonia, 0.256 Torr, 4 minutes.
Step II: Ammonia, 0.306 Torr, Plasma 40% power (RF), 2 minutes.
Step III: Ammonia, 0.256 Torr, 2 minutes.
Step IV: Ar, 0.265 Torr, 10 minutes.

To create an activated solid support, the animated plates were then reacted with 0.1 M solution of 1,1-carbonylditriazole in anhydrous AcCN with 3-5% dry triethylamine in a glove box under argon for 2-3 hours. The plates were washed three times and air dried.

The biological molecules attached to the activated solid support were 3'-amino oligonucleotide-5'-Cy3 molecules synthesized on a 3'-Amino-Modifier C7 CPG (Glen Research, Sterling, Va.) following the manufacturer's protocol on DNA synthesizer ABI 394 (Applied Biosystems, Foster City, Calif.). Cy3 is a cyanine dye which is a fluorophore, and can be purchased from Glen Research, 44901 Falcon Place, Sterling, Va. 20 ΦM of 3'-amino oligonucleotide-5'-Cy3 in bicarbonate buffer pH 9.3 with 4% $Na_2SO_4$ was deposited in about 5-25 nanoliters within a circular spot having a diameter of between about 10 microns and about 500 microns onto several sites of the plates in the form of 3×3 array by printing in a closed, dust free, and humid chamber using a Biomek 2000 device (Beckman Coulter, Fullerton, Calif.). The printed plates were left overnight in a humid chamber. Unreacted active groups were quenched with 50 mM carbonate buffer, 150 mM NaCl, 1 mg/ml casein overnight at room temperature, and then washed with water. Oligonucleotides can also be attached to microparticles in suspension using similar techniques.

Example 2

Sandwich Immunoassay with Antibodies Attached Directly on a Surface

An aminated polypropylene microwell plate with an activated solid support is prepared as in Example 1. A first set of antibodies to human cytokines IL-1b, IL-2, IL-4, and IL-8 are individually diluted into a suitable mildly alkaline printing buffer at 1-2 mg per mL and dispensed onto discrete locations within the wells of the plate using a commercial arraying instrument. A second set of antibodies to human cytokines IL-1b, IL-2, IL-4, and IL-8 are conjugated with specific oligonucleotides as described in U.S. Patent Publication No. 2003/0092901. These antibodies are specific for different epitopes compared to the first set of antibodies. Oligonucleotides complementary to those used in this conjugation can be obtained from a commercial supplier with a variety of terminal fluorescent groups.

Following an overnight incubation in a humid chamber to permit reaction, the wells of the printed plate are rinsed with Tris/Tween-20 wash buffer to remove unreacted antibody and residual reactive sites blocked with casein. Samples containing human cytokines IL-1b, IL-2, IL-4, and IL-8 are dispensed into the wells of the printed microwell plate and incubated at room temperature for 1 hour. The microwell plate is washed several times with Tris/Tween buffer to remove unbound analyte and potential interfering substances in the samples from the wells. The oligonucleotide-conjugated antibodies are added to the wells at 1-5 μg per mL in a suitable blocking buffer, such as Superblock blocking buffer (available from Pierce Biotechnology, Inc., Rockford, Ill.), and incubated at room temperature for 1 hour. The microwell plate is washed several times with Tris/Tween buffer to remove unbound oligonucleotide-conjugated antibodies.

Fluorescently labeled oligonucleotides complementary to those used in the above antibody conjugates are diluted in a suitable buffer, such as Superblock blocking buffer, and added to the wells. Hybridization is allowed to occur for one hour at room temperature, preferably in the dark. It may be necessary include additives, such as salts or organic solvents that are known in the art, to the incubation buffer in order to modulate the efficiency and fidelity of hybridization. The microwell plate is washed several times with Tris/Tween buffer to remove unhybridized fluorescent oligonucleotides.

Results can be visualized using a variety of commercial plate-based microarray readers, including Beckman Coulter Inc.'s $A^2$ reader. Spatial separation of the printed 'capture' antibodies is only necessary if the same fluorescent label is used for all oligonucleotides. Use of spectrally distinct oligonucleotide labels permits use of a mixture of capture antibodies in the test area. Alternatively, if microparticles have been utilized as a solid support the results can be read using a flow cytometer.

Example 3

Sandwich Immunoassay Using Oligonucleotide Linkers

An aminated polypropylene microwell plate with an activated solid support is prepared as in Example 1. Four amine-terminal oligonucleotides having different sequences (designated W, X, Y, and Z) are individually diluted into a suitable mildly alkaline printing buffer at 10-50 OD per mL and dispensed onto discrete locations within the wells of the plate using a commercial arraying instrument. Following an overnight incubation in a humid chamber to permit reaction, the wells of the printed plate are rinsed with Tris/Tween-20 wash buffer to remove unreacted antibody and residual reactive sites blocked with casein. These plates can be dried and stored for extended periods prior to use.

A first set of antibodies to human cytokines IL-1b, IL-2, IL-4, and IL-8 are each conjugated with a specific oligonucleotide complementary to one the oligonucleotides W, X, Y, or Z using methods described in U.S. Patent Publication No. 2003/0092901 that each type of antibody is conjugated with an oligonucleotide complementary to one of the oligonucleotides W, X, Y, or Z. These antibody conjugates are diluted to 0.1 to 5 μg per mL in a suitable blocking buffer, such as Superblock blocking buffer, and added to the wells of the printed plate in order to generate the antibody array. These are allowed to hybridize for 1 hour at room temperature. It may be necessary include additives, such as salts or organic solvents that are known in the art, to the incubation buffer in order to modulate the efficiency and fidelity of hybridization.

The microwell plate is washed several times with Tris/Tween buffer to remove unbound oligonucleotide-conjugated antibodies. Samples containing human cytokines IL-1b, IL-2, IL-4, and IL-8 are dispensed into the wells of the printed microwell plate and incubated at room temperature for 1 hour. The microwell plate is washed several times with Tris/Tween buffer to remove unbound analyte and potential interfering substances in the samples from the wells.

A second set of antibodies to human cytokines IL-1b, IL-2, IL-4, and IL-8 are conjugated with specific oligonucleotides 1, 2, 3, and 4 as described in U.S. Patent Publication No. 2003/0092901. These antibodies are specific for different epitopes than the first set of antibodies. Oligonucleotides complementary to those used in this conjugation can be obtained from a commercial supplier with a variety of terminal fluorescent groups. These oligonucleotide-conjugated antibodies are added to the wells at 1-5 μg per mL in a suitable blocking buffer, such as Superblock blocking buffer, and incubated at room temperature for 1 hour.

The microwell plate is washed several times with Tris/Tween buffer to remove unbound oligonucleotide-conjugated antibodies. Fluorescently labeled oligonucleotides complementary to those used in the above antibody conjugates are diluted in a suitable buffer, such as Superblock blocking buffer, and added to the wells. Hybridization is allowed to occur for one hour at room temperature, preferably in the dark. It may be necessary include additives, such as salts or organic solvents that are known in the art, to the incubation buffer in order to modulate the efficiency and fidelity of hybridization. The microwell plate is washed several times with Tris/Tween buffer to remove unhybridized fluorescent oligonucleotides.

Results can be visualized using a variety of commercial plate-based microarray readers, including Beckman Coulter Inc.'s $A^2$ reader. Spatial separation of the printed oligonucleotides is only necessary if the same fluorescent 'tag' is used for all labeling oligonucleotides. Use of spectrally distinct fluorescent tags permits use of a mixture of capture oligonucleotides in the test area. Alternatively, if microparticles have been utilized as a solid support the results can be read using a flow cytometer.

Example 4

Isoform-Specific Assays Using Oligonucleotide Linkers

An aminated polypropylene microwell plate with an activated solid support is prepared as in Example 1. An amine-terminal oligonucleotide is diluted into a suitable mildly alkaline printing buffer at 10-50 OD per mL and dispensed onto discrete locations within the wells of the plate using a commercial arraying instrument. Following an overnight incubation in a humid chamber to permit reaction, the wells of the printed plate are rinsed with Tris/Tween-20 wash buffer to remove unreacted oligonucleotides and residual reactive sites blocked with casein. The plates can be dried and stored for extended periods prior to use.

Antibodies to prostate specific antigen, which occurs as a number of different isoforms, are conjugated with a specific oligonucleotide complementary to the oligonucleotide dispensed onto the microwell plate using methods described in U.S. Patent Publication No. 2003/0092901. These capture antibodies are specific for an epitope that is common to all isoforms of PSA.

The conjugated antibodies are diluted to 0.1 to 5 μg per mL in a suitable blocking buffer, such as Superblock blocking buffer, and added to the wells of the printed plate in order to generate the antibody array. This is allowed to hybridize for 1 hour at room temperature. It may be necessary include additives, such as salts or organic solvents that are known in the art, to the incubation buffer in order to modulate the efficiency and fidelity of hybridization. The microwell plate is washed several times with Tris/Tween buffer to remove unbound oligonucleotide-conjugated antibodies. Samples containing the analytes as a mixture of different isoforms are dispensed into the wells of the printed microwell plate and incubated at room temperature for 1 hour. The microwell plate is washed several times with Tris/Tween buffer to remove unbound analyte and potential interfering substances in the samples from the wells.

Each member of a set of detection antibodies to isoform-specific epitopes of f-PSA, PSA-ACT, and PSA-MG is conjugated with a specific detector oligonucleotide as described in U.S. Patent Publication No. 2003/0092901. Oligonucleotides in this set have two distinct regions, one common to all labeling antibodies to a specific analyte and a second that is unique to each isoform-specific antibody. These regions can be presented as either a continuous linear strand or a branched arrangement. Oligonucleotides complementary to both regions of these sequences can be obtained from a commercial supplier with a variety of terminal fluorescent groups, however it is important that the fluor used for labeling the common region be spectrally distinct from those used for the isoform-specific regions.

These oligonucleotide-conjugated antibodies are added to the wells at 1-5 μg per mL in a suitable blocking buffer, such as Superblock blocking buffer, and incubated at room temperature for 1 hour. The microwell plate is washed several times with Tris/Tween buffer to remove unbound oligonucleotide-conjugated antibodies.

Fluorescently labeled oligonucleotides complementary to the common and isoform specific regions of the oligonucleotides conjugated to the detection antibodies are diluted in a suitable buffer, such as Superblock blocking buffer, and added to the wells. Hybridization is allowed to occur for one hour at room temperature, preferably in the dark. It may be necessary include additives, such as salts or organic solvents that are known in the art, to the incubation buffer in order to modulate the efficiency and fidelity of hybridization. The microwell plate is then washed several times with Tris/Tween buffer to remove unhybridized fluorescent oligonucleotides.

Results can be visualized using a variety of commercial plate-based microarray readers, including Beckman Coulter Inc.'s $A^2$ reader. Emission from the fluorescent oligonucleotides complementary to the common region of the labeling oligonucleotide can be used to quantitate total analyte. Fluorescent emissions for the labeled oligonucleotides complementary to the isoform specific regions of the detector oligonucleotides can be used to quantitate the different isoforms of the PSA analyte simultaneously. Alternatively, if microparticles have been utilized as a solid support, the results can be read using a flow cytometer.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A method for determining whether multiple isoforms of an analyte are present in a sample, comprising the steps of:
   (a) providing a capture agent which specifically binds multiple isoforms of the analyte at an epitope that is common to the multiple isoforms of the analyte;
   (b) providing multiple detection agents, wherein each detection agent specifically binds one of the multiple isoforms of the analyte at an epitope that is unique to the isoform of the analyte, and wherein each detection agent comprises a detector oligonucleotide comprising a first nucleotide sequence unique to the detection agent;
   (c) providing multiple first labeled oligonucleotides, each first labeled oligonucleotide complementary to the unique first nucleotide sequence of one of the multiple detection agents, wherein each first labeled oligonucleotide comprises a distinct first label;
   (d) attaching the capture agent to a solid support;
   (e) bringing into reactive contact the sample, the multiple detection agents, and the multiple first labeled oligonucleotides with the capture agent and solid support;
   (f) forming multiple complexes each comprising a first labeled oligonucleotide which is in reactive contact with the first nucleotide sequence of a detection agent which detection agent is in reactive contact with an analyte isoform which is in reactive contact with a capture agent which is in reactive contact with a solid support; and
   (g) detecting the distinct first labels in the multiple complexes formed during step (f), thereby determining whether multiple isoforms of the analyte are present in the sample.

2. The method of claim 1, wherein step (g) further comprises determining the amounts of the distinct first labels in the multiple complexes formed during step (f).

3. The method of claim 1, wherein the capture agent is attached to the solid support before the sample is contacted with the capture agent.

4. The method of claim 1, wherein the sample is contacted with the capture agent before the capture agent is attached to the solid support.

5. The method of claim 1, wherein the capture agent comprises an attachment oligonucleotide, and wherein attaching the capture agent to the solid support comprises hybridizing the attachment oligonucleotide to an oligonucleotide attached to the solid support which is complementary to the attachment oligonucleotide.

6. The method of claim 1, wherein each first labeled oligonucleotide comprises a label selected from the group consisting of a light-emitting compound, a dyed microparticle, a fluorescent protein, a fluorescent nanocrystal, a metal sol, an enzyme, an enzyme substrate, an enzyme cofactor, an enzyme inhibitor, a spin label, a chelating compound, a mass label, and a radioactive isotope.

7. The method of claim 1, further comprising the step of bringing into reactive contact the multiple detection agents with multiple second labeled oligonucleotides, each second labeled oligonucleotide comprising a second label, wherein the detector oligonucleotide of each detection agent further comprises a second nucleotide sequence, wherein each second labeled oligonucleotide is complementary to the second nucleotide sequence of one of the multiple detection agents, and wherein each second label is different from any one of the first labels.

8. The method of claim 7, wherein, when one of the multiple first labeled oligonucleotides and one of the multiple second labeled oligonucleotides are complementary to and bound to the first and second nucleotide sequences of one of the multiple detection agents, a Förster resonance energy transfer interaction can occur between the first label and the second label.

9. The method of claim 7, wherein each detector oligonucleotide is a branched oligonucleotide comprising a first side chain and a second side chain, and wherein for each detection agent one of the multiple first labeled oligonucleotides is complementary to the first nucleotide sequence of the first side chain and one of the multiple second labeled oligonucleotides is complementary to the second nucleotide sequence of the second side chain of the same detector oligonucleotide.

10. The method of claim 7, wherein the second nucleotide sequences of the multiple detection agents are identical, and wherein the multiple second labeled oligonucleotides comprise identical second labels and are complementary to and bound to the identical second nucleotide sequences of the multiple detection agents, further comprising the step of detecting the amount of the second labels in the multiple complexes formed during step (f), thereby determining the total amount of the multiple isoforms of the analyte present in the sample.

11. The method of claim 1, wherein the capture agent is an antibody.

12. The method of claim 1, wherein each detection agent is an antibody.

13. The method of claim 1, wherein the solid support is selected from the group consisting of a planar surface, a fiber, a capillary, and a particle.

14. The method of claim 1, wherein step (g) comprises detecting the labels with a detector selected from the group consisting of a microwell plate reader, a flow cytometer, a fluorometer, and a mass spectrometer.

15. The method of claim 1, wherein the multiple isoforms of the analyte are two isoforms of the analyte, each isoform specifically bound by a first or second detection agent, wherein the detector oligonucleotides of the first and second detection agents comprise a common second nucleotide sequence, further comprising the steps of:
   (h) providing an additional labeled oligonucleotide complementary to the common second nucleotide sequence, wherein the additional labeled oligonucleotide comprises an additional label; and
   (i) bringing into reactive contact the additional labeled oligonucleotide with the first detection agent and the second detection agent.

16. The method of claim 15, further comprising the step of determining the amount of the additional label in the multiple complexes formed during step (i), thereby determining the combined amount of the first isoform and the second isoform of the analyte in the sample.

17. The method of claim 15, wherein a Förster resonance energy transfer interaction can occur between one of the first labels and the additional label, when one of the multiple first labeled oligonucleotides and the additional labeled oligonucleotide are complementary to and bound to the same detector oligonucleotide.

18. The method of claim 15, wherein each detector oligonucleotide is a branched oligonucleotide comprising a first side chain and a second side chain, and wherein one of the multiple first labeled oligonucleotides is complementary to and bound to the first nucleotide sequence of the first side chain of a detector oligonucleotide, and wherein the additional labeled oligonucleotide is complementary to and bound to the second nucleotide sequence of the second side chain of the same detector oligonucleotide.

* * * * *